(12) United States Patent
Wellnhofer (10) Patent No.: US 7,264,593 B2
(45) Date of Patent: Sep. 4, 2007

(54) METHOD FOR DETERMINING, MONITORING AND UPDATING CORRECTION DATA FOR LIQUID-FILLED TRANSMISSION SYSTEMS

(75) Inventor: Ernst Wellnhofer, Berlin (DE)

(73) Assignees: Deutsches Herzzentrum Berlin, Berlin (DE); Medserv GmbH, Leipzig (DE)

( * ) Notice: Subject to any disclaimer, the term of this patent is extended or adjusted under 35 U.S.C. 154(b) by 631 days.

(21) Appl. No.: 10/381,942

(22) PCT Filed: Sep. 25, 2001

(86) PCT No.: PCT/DE01/03719

§ 371 (c)(1),
(2), (4) Date: Aug. 18, 2003

(87) PCT Pub. No.: WO02/26127

PCT Pub. Date: Apr. 4, 2002

(65) Prior Publication Data

US 2004/0024294 A1 Feb. 5, 2004

(30) Foreign Application Priority Data

Sep. 28, 2000 (DE) .................... 100 49 734

(51) Int. Cl.
*A61B 5/00* (2006.01)
(52) U.S. Cl. ..................................... 600/486; 60/488
(58) Field of Classification Search ................ None
See application file for complete search history.

(56) References Cited

U.S. PATENT DOCUMENTS 4,232,373 A * 11/1980 Jackson et al. ............... 702/70
4,325,382 A * 4/1982 Miodownik ................ 600/486
5,827,195 A 10/1998 Lander
6,290,652 B1 9/2001 Wellnhofer

FOREIGN PATENT DOCUMENTS

DE 198 20 844 A1 6/1999

OTHER PUBLICATIONS

International Search Report of PCT/DE01/03719, dated Mar. 6, 2002.
English Translation of international Preliminary Examination Report of corresponding International Application No. PCT/DE01/03719, dated Dec. 27, 2002.

* cited by examiner

*Primary Examiner*—Robert L. Nasser
(74) *Attorney, Agent, or Firm*—Christie, Parker & Hale, LLP.

(57) ABSTRACT

Method for determining, monitoring and updating correction data for correcting measured value distortions and for calibrating liquid-filled transmission systems, via which signals from the patient detected in the body of a patient are transmitted to an external measured value receiver, in particular for invasive pressure measurements in cardiology, intensive care medicine and anaesthesia. The correction data are determined in the frequency range for each frequency from statistics of the signals from the patient measured at this frequency, in particular from the transmission function obtained from the signal from the patient. In the determination of the correction data, empirically checked assumptions about the corresponding statistics of undistorted signals from the patient and general properties of the transmission function are used.

31 Claims, 7 Drawing Sheets

METHOD FOR DETERMINING, MONITORING AND UPDATING CORRECTION DATA FOR LIQUID-FILLED TRANSMISSION SYSTEMS

CROSS-REFERENCE TO RELATED APPLICATION

This application is a national Phase Patent Application of International Application Number PCT/DE01/03719, filed on Sep. 25, 2001, which claims priority of German Patent Application Number 100 49 734.9, filed on Sep. 28, 2000.

BACKGROUND

The invention relates to a method for determining, monitoring and updating correction data for correcting measured value distortions and for calibrating liquid-filled transmission systems.

Liquid-filled transmission systems may be used for invasive intra-arterial and intravenous pressure measurement in cardiology, intensive care medicine and anaesthesia. In these systems the pressure measurement takes place in the body of a patient and is transmitted via the liquid-filled transmission system formed as a catheter to a pressure transducer arranged outside the body of the patient. As a function of the length, cross-section, construction, the elastic material properties of the catheter and the composition of the liquid located in the catheter, various resonances, dampings and energy losses of the measured value of the pressure detected as a signal from the patient at the end of the catheter inside the body occur and lead to substantial distortions of this signal from the patient owing to the fluid-filled transmission system. These distortions do not allow any quantitative analysis of the signals from the patient and impair the qualitative interpretation of the diagnosis and monitoring.

To avoid distortions of the signals from the patient owing to the liquid-filled transmission system pressure measuring transducers known as tip pressure sensors were arranged at the tip of the catheter serving as the liquid-filled transmission system and the signal detected from the patient converted into an electrical signal and guided from the body of the patient via an electrical line. Tip pressure sensors of this type are very expensive, however, and only available to a limited extent with respect to their shape and size.

A method for computer correction of measured value distortions by the liquid-filled transmission system in the transmission of a signal from the patient measured inside the body of a patient is known from DE 1 982 208 844 A1. In this reference the electrical signal from the (distorted) signal from the patient emitted by the external pressure transducer is guided through an analogue/digital transducer and the digitalised signal emitted is analysed in a signal analysis and processing unit operating on the basis of a digital Fourier analysis and carrying out a beat by beat analysis of the digitalised signal. The analysed signal is then linked with empirically determined correction data called up from a correction data record matrix or as a correction data record vector and output as Fourier coefficients. The signal corrected by the signal analysis and processing unit is finally guided to an output and/or evaluation unit.

The correction data record required for this known method can be determined inter alia from a reference pressure measurement. In order to determine the transmission function, instead of the unknown measured signal, here an artificially generated known test pressure signal can be input as the reference signal, from the distortion of which the properties of the transmission system can then be concluded.

One possibility is to obtain a calibration data record from a calibrator arranged on the catheter tip, but this necessitates the maintenance of sterile conditions, causes awkward handling and means that changes in the transmission function have to be taken into account as, for example, the catheter guided to the pressure measuring site and calibrator is rinsed, medication is supplied via the catheter and so-called "microbubbles" change the transmission function. If such changes take place, recalibration is required which, however, is not easy to carry out in the case of a horizontally located catheter, in other words in a catheter located in the body of the patient.

A further possibility is to obtain a correction data record from the transmission function by means of an external calibration signal. For this purpose a calibration signal in the form of a jump signal, a pressure impact or a noise is transmitted at the side of the catheter remote from the measuring position, in other words outside the body of the patient, and the inherent oscillation produced in the process is used to calculate the correction data record. However, a plurality of problems occur in this type of determination of the transmission function by means of an external calibration signal. On the one hand, the calibration signal, i.e. the jump signal, the pressure impact or the noise have to be generated very precisely and in a reproducible manner and this necessitates measurements over a fairly long time period owing to the inconstant measuring behaviour of the transmission system and therefore cannot be implemented, for example in a hospital, owing to the high time and training input. On the other hand, use of an automatic mechanical device mounted to the pressure transducer, is very expensive and moreover, as a mechanical precision part, required special servicing for setting up and maintenance.

There is the additional problem of signal separation during calibration in a horizontal catheter, as otherwise the measured jump response to a jump signal by the actual signal from the patient, for example a blood pressure signal is too greatly distorted and therefore incorrect correction data records are determined. The resultant dependency of the instant of the resolution of the jump signal, impact on the system or noise substantially restricts the reproducibility and causes substantial effort in particular in the case of irregular signals from the patient.

A method for reducing the noise in an ECG signal is known from U.S. Pat. No. 5,827,195, in which a pulse sequence corresponding to the heartbeat is selected and is converted into a multi-dimensional display using a brief Fourier transformation for evaluating the time/frequency display. In addition, a multi-dimensional filter function is used on the multi-dimensional display of the pulse sequence to thus raise the signal-to-noise ratio of the pulse sequence. The statistical attempts used in the process to correct the ECG signal pulse sequence only serve to eliminate simple disturbances in the pulse sequence, however, which can be assumed to be normally distributed and of which the band width can easily be separated from the band width of the useful signal.

SUMMARY

One embodiment of the present invention relates to a method of the type mentioned at the outset which allows continuous monitoring and on-going updating of calibration data for a correction of measured value distortions of a signal from a patient without an external calibration signal and ensures a robust correction method which is not prone to faults with respect to artifacts and other disruptions contained in the measured signals.

This may be achieved according to the invention by a method with the features of claim 1.

The correction coefficients for a correction of measured value distortions in the frequency range for each frequency line are determined from statistics of the signals measured at this frequency. In the process empirically checked assumptions about the corresponding statistics from undistorted signals from patients and general properties of the transmission function are used. The achievement according to this embodiment of the invention allows determination, continuous monitoring and ongoing updating of the calibration data record for correcting the measured value distortions of signals from the patients without an external calibration signal and creates an economical correction method which is substantially easier to operate and to service compared to an external calibration device and is less prone to disruptions. The transmission function in the correction method being determined directly from the patient's signal.

As advantageous configuration of the solution according to this embodiment of the invention is characterised in that the correction data are determined from the transmission function determined from the signal from the patient and in that in the determination of the correction data empirically checked assumptions about the corresponding statistics of undistorted signals from patients and general properties of the transmission function are used.

The solution according to this embodiment of the invention allows the following procedure for determining, monitoring and updating the transmission function in the frequency range to obtain therefrom calibration data records, without an external calibration apparatus:

1. A (pressure) signal from the patient measured invasively by conventional catheter systems serves as the input signal. A possible variation to this is the use of the derived function of the pressure signal according to time instead of the original signal.
2. A segmentation of the signal then follows, either heartbeat by heartbeat or in the form of segments of signals from the patient which are suitable for a Fourier transformation with respect to their length. Suitable means here inter alia that from a minimum length, the sign change of the first derived function of the pressure according to time under the boundary condition of a minimum amount of the second derived function of the pressure according to time is sought. A further option for determining the suitable length is that from a minimum length, the minimum of the error in approximation of the pressure signal is determined by a Fourier series cut off in the higher frequency range. Further optional preprocessing steps are a linear trend adjustment and a multiplication of the segment.
3. There follows a complex Fourier transformation of the segments matched to the segment length and a transformation by means of zero padding in the case of a fast Fourier transformation.
4. The attempt to determine the transmission function is based on segment by segment statistics of the complex Fourier coefficients determined under Item 3. The signal model for a complex Fourier coefficient $S_i$ is, as the convolution presents a complex multiplication in the frequency range:

$$S_i = t_i(m_i + v_i)$$

With $t_i$ as the multiplicative component (convolution with transmission function), $m_i$ as the mean and $v_i$ as the variable portion of the Fourier coefficient $S_i$ determined from the measurement of the signal from the patient for the frequencies $i=0 \ldots$ maximum. The number n of the segments or the segment by segment Fourier transformation for the statistics is determined such that $(m_n - m_{n-1})^2 < \epsilon$ (mean value stability) and $\Sigma(s_j - m_n)^2 > \delta$ (adequate variance for statistics) with $m_n$ the mean value of the complex Fourier coefficient in statistics of length n and $s_j$ the complex value of the Fourier coefficient in a repetition j with $j=1 \ldots n$ and $\epsilon$ and $\delta$ as selected bounds. The optimum threshold values $\epsilon$ and $\delta$ have to be determined empirically here.
5. The following general assumptions about the signal from the patient are therefore used as a whole or partially for determining the transmission function. A good approximation is adequate for all the assumptions:
   5.1 The transmission function remains constant over the time period for the statistics.
   5.2 The signal from the patient contains a component which is variable even over short periods and is not strictly periodic.
   5.3 The transmission function up to the first resonance corresponds to a second-order system.
   5.4 The transmission function corresponds to the identity in the frequency range 1-2 Hz.
   5.5 The transmission function can be ignored in the range of very high frequencies with amplitudes $< \epsilon$ (noise virtually zero).
6. The transmission function is determined from the statistics of the form $$[\Sigma(s_{ij}-m_j)^p]/[\Sigma(s_{ij}-m_j)^q] \text{ or } (m_j)^p/m_j)^q$$

for all the frequency lines $j=1 \ldots$ maximum and for $i=1 \ldots n$ segments. For the parameters p and q, $p>q$ applies.

Instead of mean values median values can also be used to stabilise the statistics with respect to freak values. A statistic of this type can be regarded according to the signal model as a sequence of complex Fourier coefficients. A derived sequence of coefficients with more uniform size distribution over the frequency range is obtained by complex differentiation or logarithmisation of the corresponding Fourier sequence. Furthermore, the parameters p and q are empirically determined. The special case $p=1$ and $q=0$ is permitted, for example for $p=3$ and $q=2$ it applies that with undistorted signals from the patient, the real part of the logarithm of the statistics $$[\Sigma(s_{ij}-m_j)^3]/[\Sigma(s_{ij}-m_j)^2]$$

for all the j's decreased linearly with the logarithm of the frequency. A variation is the additional determination of higher-order moments and cumulants to improve the signal model by characterizing the distribution of the exciting signal.
7. The ratio of the actual statistics to the statistics to be expected in an undistorted signal from the patient or the weighted difference of these functions after logarithmic transformation is investigated to determine the transmission function. The determination of the cepstrum (homomorphic deconvolution) provides a possible variation for combination of the Fourier transformation according to Item 3 and the logarithmic transformation.
8. To reduce the noise in these statistics the following methods can be used individually or in combination:
   8.1 an (optionally weighted) averaged summation of a plurality of consecutive determinations of the transmission function according to Item 7.

8.2 a slight coarsening of the spectral resolution by class formation for a plurality of frequency lines, 8.3 a flattening interpolation or use of a median or low-pass filter. There may also be a direct adaptation to a second-order system or another flat function, for example a spline function, with minimum deviation of the noisy transmission function determined from the statistics.

9. The damping coefficient and the resonance frequency or the amount of the transmission function for the individual frequency lines can be determined from the results under Item 8.

As an alternative the resonance frequency can be determined directly from statistics of the form described under Item 6. This method allows an estimation of the damping. The logarithms of the mean values, for example and still better those of the medians correlate with the frequency. The gradient in the corresponding regression in the case of distorted signals from patient supplies an estimated value for the damping. The absolute amounts of the medians of higher frequencies are also smaller in the case of stronger damping. A plurality of estimated values for the resonance frequency and damping can be averaged with weighting with respect to their quality or combined by means of multiple regression models. Corresponding regression models may also be non-linear. Parameters for corresponding models can be determined from systematic in-vitro test series. Very stable and precise estimation of resonance frequency and damping can thus be obtained.

10. An iterative method with respect to items 7 to 8 can optionally be carried out to improve the results.

11. The phase can then be clearly calculated from the transmission function with the assumption of a second-order system or determined from further statistics of the form specified under Item 6, wherein the developed phase of the statistics in the form $[\Sigma(s_{ij}-m_j)^3]/[\Sigma(s_{ij}-m_j)^2]$ in the case of undistorted signals from patient shows, in particular, a sigmoidal systematic relationship to the frequency.

12. The complex inverse of this function is clearly determined by computer from the amplitude and the phase of the transmission function determined in this way. This inverse is the correction data record for a correction in the frequency range, a segment by segment Fourier transformation of the measured pressure signals according to items 1 to 3 taking place.

BRIEF DESCRIPTION OF THE DRAWINGS

The concept on which the invention is based will be described in more detail with the aid of the embodiments and curve shapes shown in the drawings, in which.

DETAILED DESCRIPTION

Figure 1:
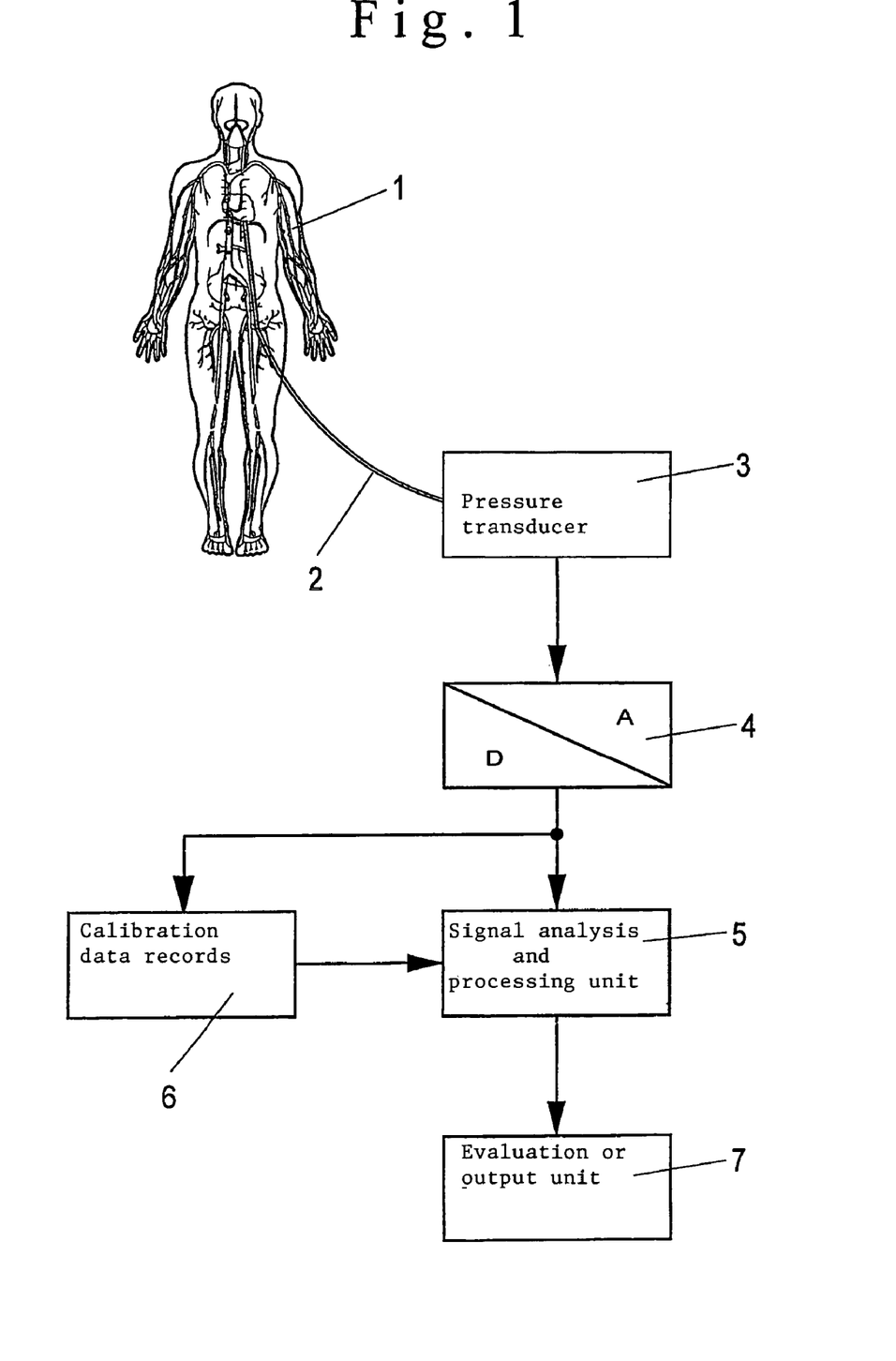
FIG. 1 shows a functional diagram of an apparatus for blindly determining the transmission function of a liquid-filled system of signals from the patient convoluted with the transmission function for the determination, monitoring and updating of correction data for correcting measured value distortions and for calibrating liquid-filled transmission systems.

FIG. 1 shows a basic structure of an invasive pressure measurement by means of a liquid-filled transmission system. A catheter 2 forming the liquid-filled transmission system is moved in the venous or arterial system of a patient 1 close to the point at which the system is to be measured. For example, for the impedance at the arterial vessel system, the catheter 2 is positioned close to where the pressure or a derived function of the pressure according to time is to be measured for measurement of the isovolumic contraction force or the like. To influence the patient 1 as little as possible by the catheter 2, the catheter 2 has dimensions which are as small as possible and consists preferably of an elastic material and is formed in a hose-like manner. Located at the tip of the liquid-filled catheter 2 is an aperture, through which, for example, pressure pulses are picked up and passed on by the catheter 2 and a line which is also liquid-filled, to a pressure transducer 3.

The pressure transducer 3 generates electric signals as a function of the pressure pulses which signals may be shown or evaluated accordingly. This method has been known in principle for a long time. A possible correction of the transmission function of this transmission system took place after determination of the resonance frequency and the damping coefficient by means of a similar electrical circuit or a corresponding numerical algorithm.

To effectively correct the measurement distortions in the range up to 40% occurring with use of the above-described method, in the method according to the invention an analogue/digital converter 4 is arranged between the pressure transducer 3 and a signal analysis and processing unit 5. The converter 4 converts the analogue signals of the pressure transducer 3 into digital signals that are applied at the input of the signal analysis and processing unit 5. In the signal analysis and processing unit 5 the measured data are loaded with correction factors on the basis of a digital Fourier analysis. The measured values corrected in this way are passed to an output or evaluation unit 7.

A device for determination, continuous monitoring and updating of calibration data records 6 for correction of measured value distortions of the pressure signal is connected to the output of the analogue/digital converter 4 and may be connected to the signal analysis and processing unit 5. Device 6 determines, monitors and updates parameters of the catheter line system and the correction factors. The digitalised signals loaded with corrected Fourier coefficients are transferred from the signal analysis and processing unit 5 to a display or evaluation unit 6, wherein a display can take place both on a monitoring system and on a print-out. Depending on the standard of the monitor, the signals are initially supplied to a digital/analogue converter and then output or relayed directly to a monitor which can process digital signals. The signals optionally have to be processed in such a way that there is a suitable format for display.

Another embodiment relates to the transfer of the data to a computer which stores and evaluates it. In this case the data are not processed in a digital/analogue converter but directly passed on from correction.

Another embodiment relates to carrying out correction not on line, but storing the data for evaluation or correction as a later time. The prerequisite for this is the availability of system-specific data and of information about the measuring conditions so an appropriate selection of the correction data records can take place subsequently. The data are advantageously picked up for this directly following the pressure transducer 3 and placed on a suitable storage medium, for example a CD or diskette.

Figure 2:
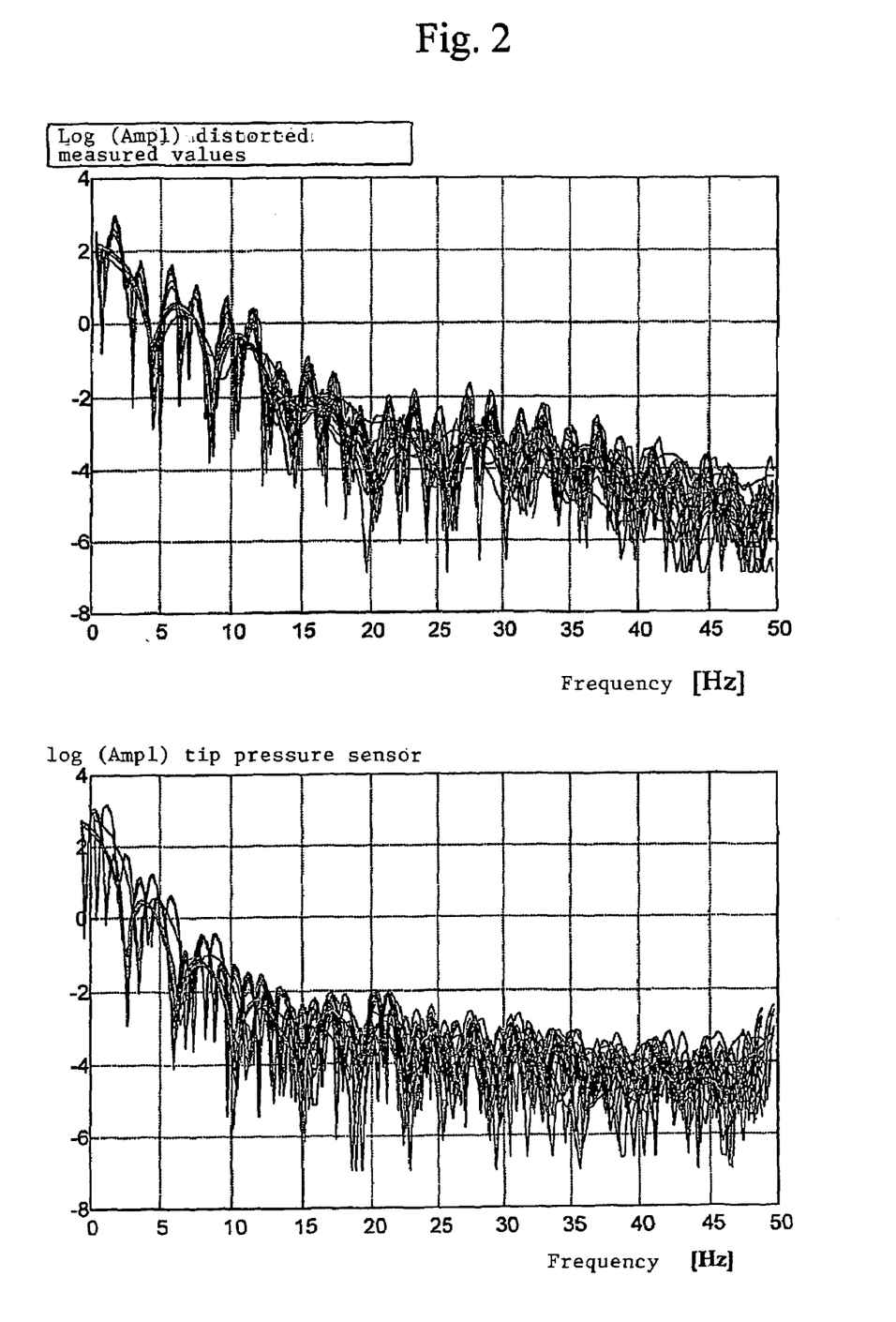
FIG. 2 shows graphical representations of the superpositioned spectra of a plurality of measurements of the logarithm of the amount of statistics in measurements with tip pressure sensors and measurements with measured values distorted by a liquid-filled system.

FIG. 2 shows the curve shape of the superpositioned spectra of a plurality of measurements of the logarithm of the amount of the statistics (=real part of the complex logarithm of the statistics) $[\Sigma(s_{ij}-m_j)^3]/[\Sigma(s_{ij}-m_j)^2]$. The lower graphics show the curve shape for tip pressure curves and the upper graphics show the measured values distorted by a liquid-filled system. The exponential drop in the tip pressure curves which becomes a linear drop in a logarithmisation of the frequency axis can clearly be seen. The corresponding statistic of the measured values distorted by the liquid-filled transmission system deviates significantly from this exponential drop. This difference in the spectra of the tip pressure curves and the measured values distorted by the liquid-filled transmission system is the result of the transmission function.

The transmission function can therefore be determined when the curves shown in the lower diagram can be adequately determined from the curves shown in the upper diagram. It basically applies that independently of the type of illness, the exponential fit of the measured pressure and the individual measurement is very good for all undistorted pressure measurements of the patient (r>0.9). This relationship empirically checked on an extensive data record is the basis for the estimation of the shape of the statistics for tip pressure curves from the corresponding statistics for the measured values distorted by the liquid-filled transmission system.

Figure 3:
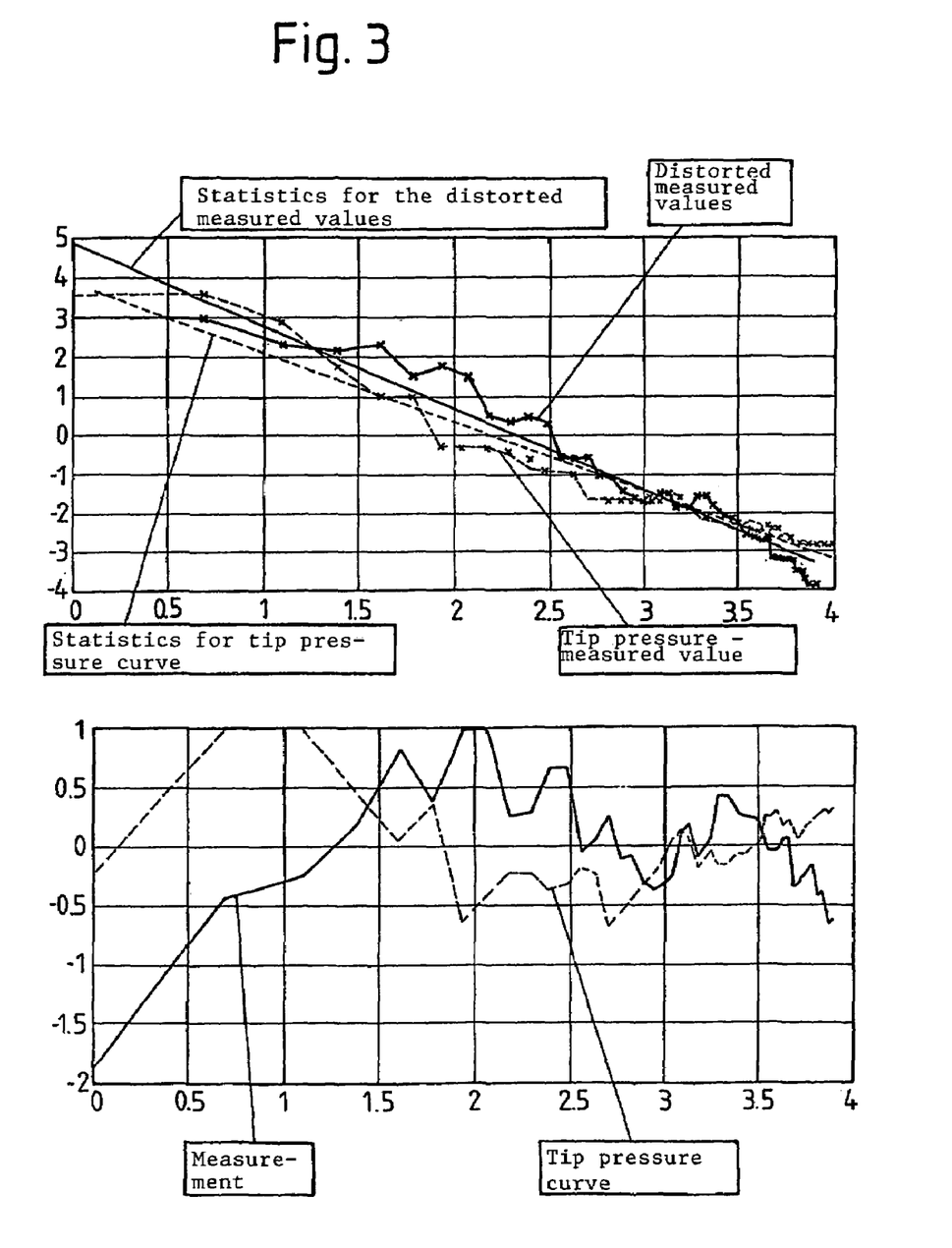
FIG. 3 shows a graphical representation of the spectra of a measurement of the logarithm of the amount of statistics in measurements with tip pressure sensors and measurements with measured values distorted by a liquid-filled system with respective logarithmised frequency axis.

FIG. 3 shows in the upper representation the spectra of a measurement of the logarithm of the amount of the statistics (=real part of the complex logarithm of the statistics)

$$[\Sigma(s_{ij}-m_j)^3]/[\Sigma(s_{ij}-m_j)^2]$$

for a tip pressure curve and corresponding statistics for the measured values distorted by the liquid-filled transmission system. The frequency axis is logarithmised (natural logarithm). The discrepancy in the range of the transmission function can clearly be seen.

The corresponding regressions for the tip pressure curve and the measured values distorted by the liquid-filled transmission system is shown in the lower illustration. This clarifies the problem of determining the regression for the tip pressure curves from the curve of the distorted measured values. This is not done with a simple regression as the gradient and offset of the two curves do not agree. The corresponding attempts to process this problem are explained in conjunction with FIG. 4.

In the analysis of the residues after subtraction of the regressions the peak caused by the transmission function in the range of the resonance frequency can clearly be seen in the residues of the distorted measured values. The residues of the tip pressure curve oscillate in the range of the higher frequencies around the zero line but in the range of the lower frequencies show a significant peak caused by the forceful base oscillation and the first upper oscillations of the pulse signal and has to be taken into account in setting up a signal model.

Figure 4:
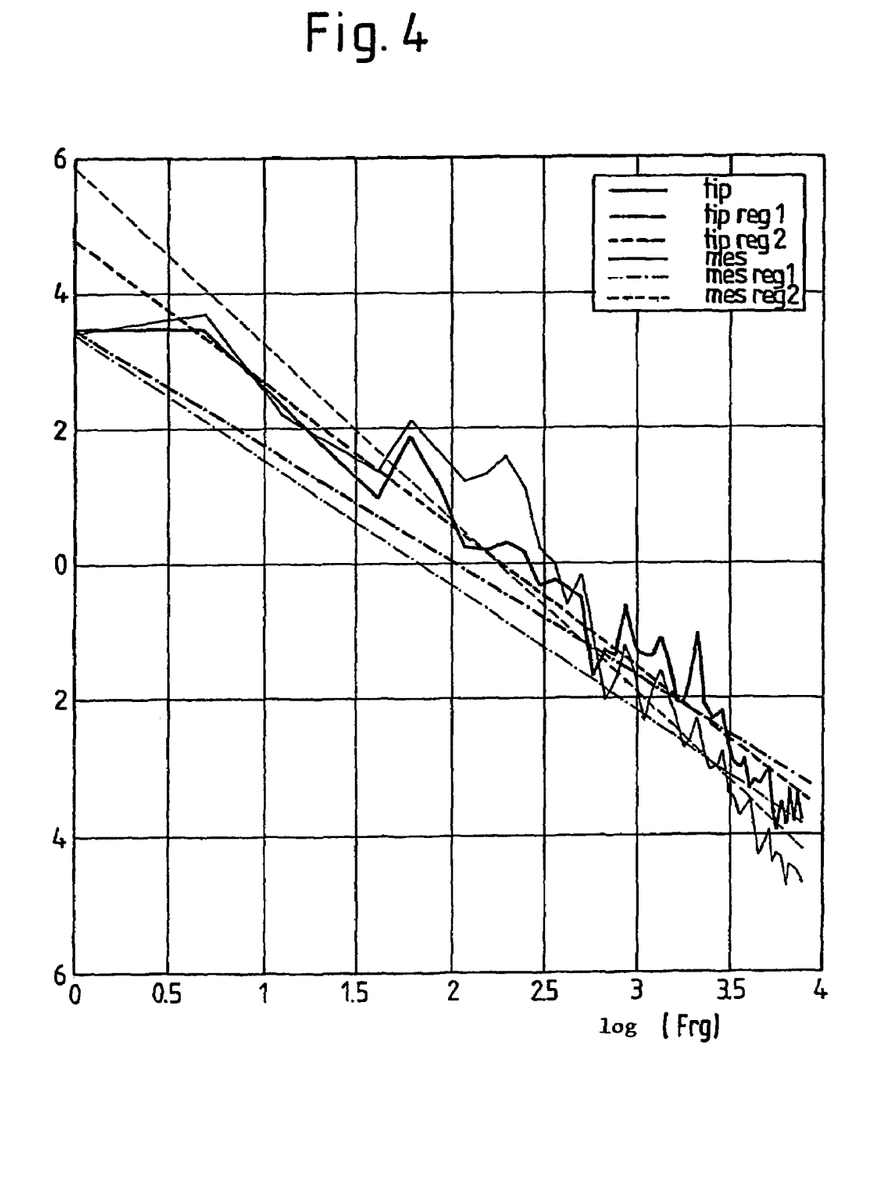
FIG. 4 shows a graphical representation of the spectra of a measurement of the logarithm of the amount of the statistics, in measurements with tip pressure sensors and measurements with measured values distorted by a liquid-filled system with respective logarithmised frequency axis and with regressions for the curve shape in the measurement with tip pressure sensors and in measured values distorted by a liquid-filled system.

FIG. 4 shows the spectra of a measurement of the logarithm of the amount of the statistics (=real part of the complex logarithm of the statistics)

$$[\Sigma(s_{ij}-m_j)^3]/[\Sigma(s_{ij}-m_j)^2]$$

for a tip pressure curve (tip) and corresponding statistics for the measured values (mes) distorted by the liquid-filled system. The frequency axis is logarithmised for this purpose (natural logarithm).

The corresponding regressions for the tip pressure curve (tip reg 1 and tip reg 2) and for the measured values distorted by the liquid-filled system (mes reg 1 and mes reg 2) are the two upper lines which intersect in the centre of the figure. Using the assumptions that the transmission function in the lower frequency range corresponds to the identity (Item 5.4 of the above feature breakdown) and can be ignored when a certain signal threshold is not reached (Item 5.5 of the above feature breakdown), a type of two-point regression may be formed (see the two lower straight lines in FIG. 4).

In the absence of a tip pressure reference measurement (normal measuring case) the two curves representing the distorted measured values and the regressions of the distorted measured values are available. The curve representing the tip pressure measurement should be estimated. This occurs adequately with a weighted averaging of the two regressions of the distorted measurement.

This estimation can be iteratively improved by rough estimation of the resonance frequency. This step is also extensively checked empirically.

Figure 5:
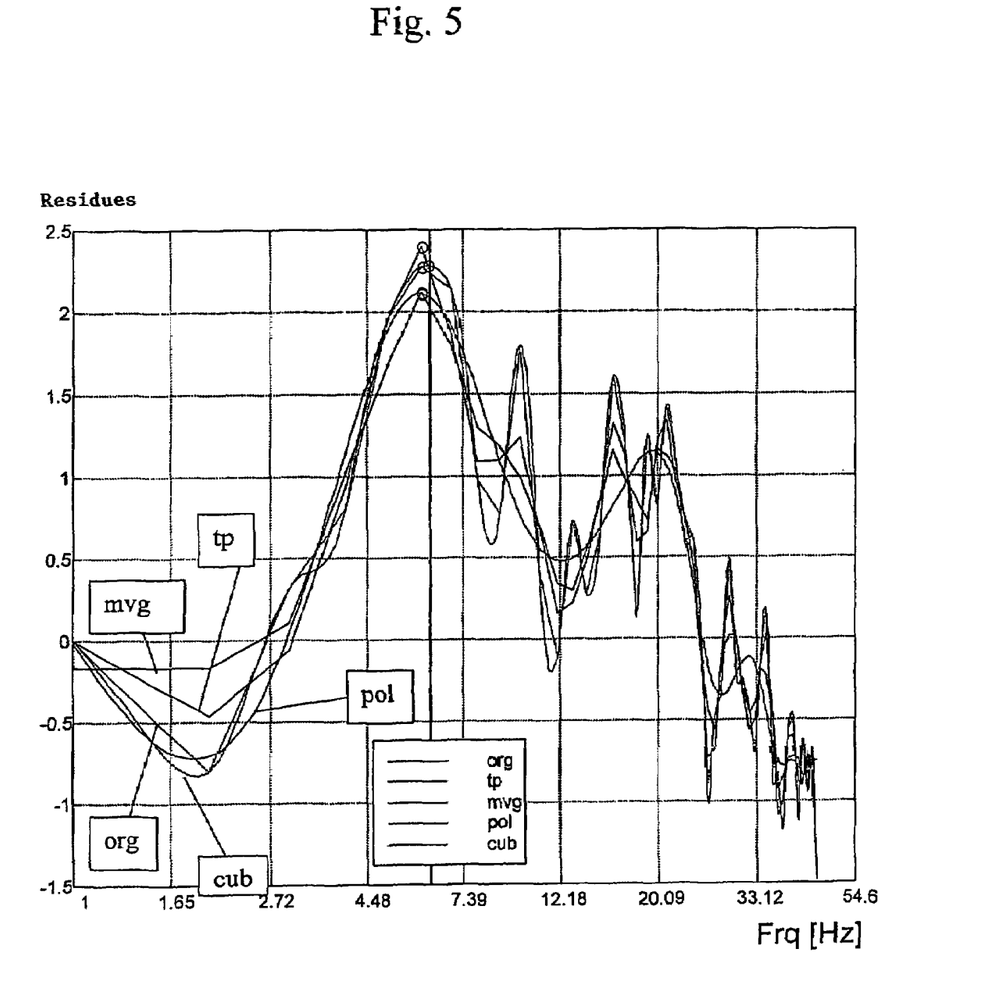
FIGS. 5 and 6 show a graphic representation of the residues flattened by various methods, of measurements of the logarithm of the amount of resonances independently determined with external calibration for two different liquid-filled systems
Figure 6:
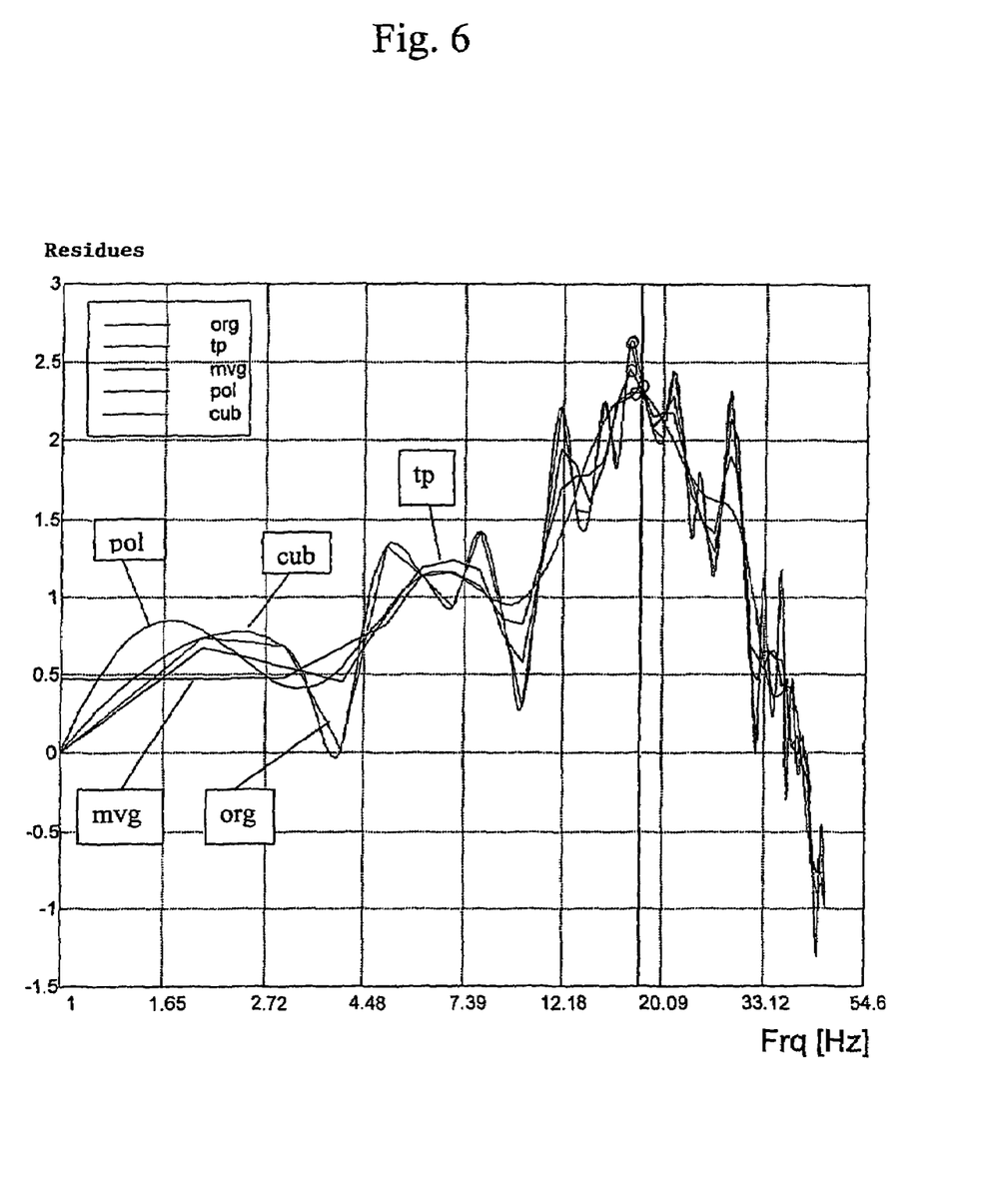

FIGS. 5 and 6 show the residues flattened by various methods, of measurements of the logarithm of the amount of the statistics (=real part of the complex logarithm of the statistics)

$$[\Sigma(s_{ij}-m_j)^3]/[\Sigma(s_{ij}-m_j)^2]$$

for two different liquid-filled systems with resonances independently determined by external calibration.

In FIGS. 5 and 6:

"org" designates the original measurement, i.e. the unprocessed measuring curve, "tp" the curve flattened by means of a low-pass filter, "mvg" designates the curve flattened by a mean value filter, "cub" the curve flattened by interpolation by a cubic polynomial "pol" designates the curve filtered with a general polynomial.

The flattening carried out by a low-pass filter proved in the process to be the most stable. The empirically determined resonances are marked by rings. The frequency axis is logarithmised but inscribed with corresponding delogarithmised frequencies.

Figure 7:
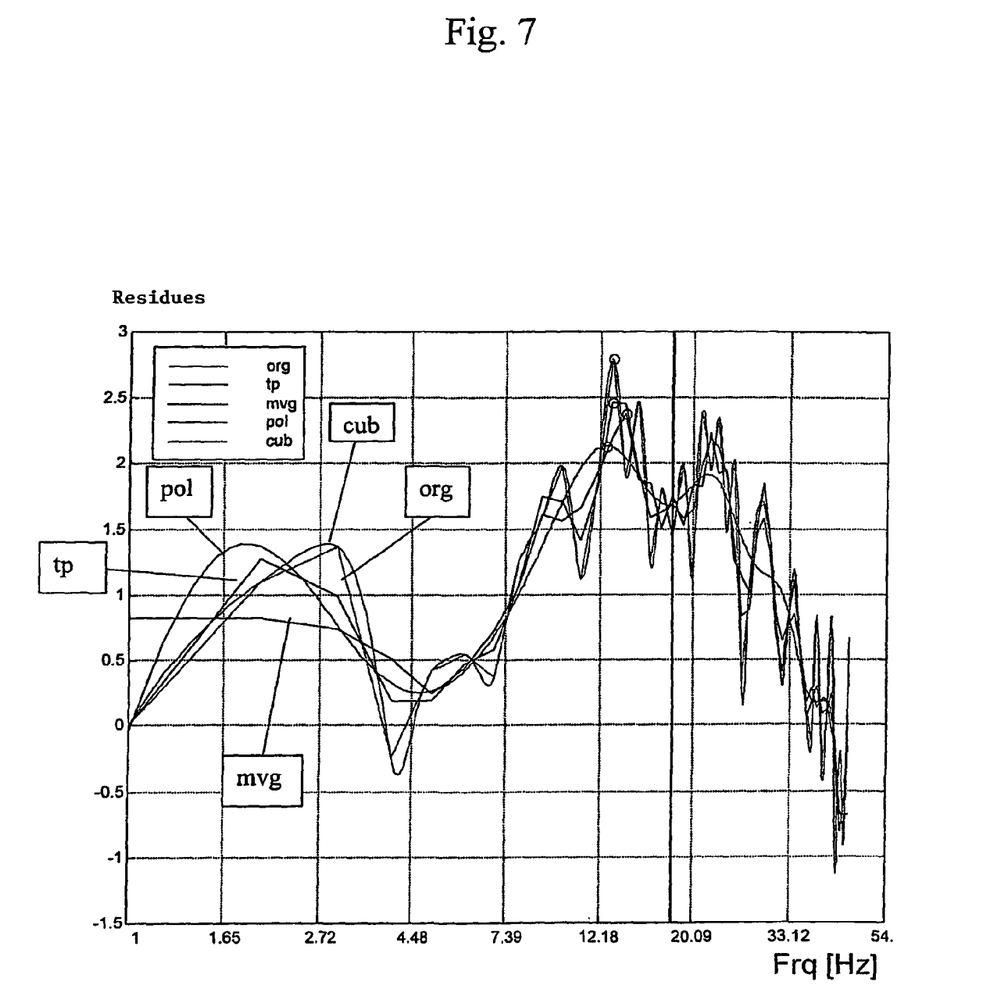
FIG. 7 shows a graphic representation as in FIGS. 5 and 6 with empirically determined resonances.

The result can be seen according to FIG. 7, in which curve shapes are shown corresponding to FIGS. 5 and 6 and are correspondingly designated, but in measurements with a relative gap in the spectrum of the excitation signal (tip signal, reference signal) are disrupted in the region of the resonance frequency. An improved interpolation method, for example fitting to a second-order system eliminates this problem.

A further, possibly disruptive problem is the peak in the region of the low frequencies of the original signal caused by the forceful base oscillation and the first upper oscillations of the pulse signal. This problem can be overcome as follows:

1. By establishing a lower limit for a plausible resonance frequency, for example 3 Hz.
2. By setting to zero the residues in the lower frequency range (up to 1 (2) Hz) 0.
3. By improving the model such that the start of the estimated reference regression is replaced by the measured values with the assumption that the transmission function is the identity in the lower frequency range. To ensure constancy it is expedient to average the two curves weighted, the weight of the measured value at 1 Hz being 1 and falling relatively quickly to 0, and the weight of the regression at 1 Hz being 0 and rising relatively quickly to 1.

Even without these improvements (fitting to second-order system, and improvement of the signal model) the method allows exact determination of the damping coefficient and resonance frequency independently of the patient (symptoms), type of pressure and transmission system, as could be proven in systematic comparison investigations with transmission function determined independently by external calibration.

What is claimed is:

1. Method for determining, monitoring and updating correction data for correcting measured value distortions caused by a liquid-filled transmission system and for calibrating the liquid-filled transmission system, as in invasive pressure measurements in cardiology, intensive care medicine and anaesthesia, the method comprising:
   measuring signals from a patient using the liquid-filled transmission system,
   generating spectral statistics of the measured signals from the patient, and
   determining correction data in a frequency range using logarithmic transformations for each frequency from the spectral statistics of the measured signals from the patient.

2. Method according to claim 1, wherein the correction data are determined from a transmission function obtained from the signals from the patient.

3. Method according to claim 2, wherein in determining the correction data, empirically checked assumptions about corresponding statistics of distorted signals from the patient and general properties of the transmission function are used.

4. Method according to claim 2, comprising:
   a) segmenting the measured signals from the patient,
   b) performing a complex Fourier transformation of the segments matched to segment length,
   c) determining segment by segment statistics of complex Fourier coefficients determined by the complex Fourier transformation, and
   d) determining the transmission function from a ratio of the segment by segment statistics of the complex Fourier coefficients determined to statistics of complex Fourier coefficients to be expected in an undistorted signal from the patient.

5. Method according to claim 4, wherein the complex Fourier transformation of the segments matched to the segment length comprises a fast Fourier transformation by means of zero padding.

6. Method according to claim 4, wherein the segmentation takes place in signal from the patient segments which are suitable with respect to their length for a Fourier transformation.

7. Method according to claim 6, wherein a length of the signal from the patient segment suitable for the Fourier transformation is determined in that from a presettable minimum length, a sign changed of a first derived function of the measured signal from the patient occurs according to time with a boundary condition of a minimum amount of a second derived function of the signal from the patient according to time.

8. Method according to claim 6, wherein a length of the signal segment from the patient suitable for the Fourier transformation is determined in that from a presettable minimum length, a minimum fault occurs in approximation of the signal from the patient by a Fourier series cut off in a higher frequency range.

9. Method according to claim 4, comprising a trend adjustment of the segmentation of the signal from the patient or pressure signal from the patient.

10. Method according to claim 4, comprising a multiplication of the segmented signal from the patient or pressure signal from the patient.

11. Method according to claim 4, wherein a signal model for a complex Fourier coefficient $S_i$ is $$S_i = t_i(m_i + v_i),$$

wherein $t_i$ is at most a multiplicative component, $m_i$ is a mean value and $v_i$ is a variable portion of the Fourier coefficient $S_i$ determined from a measurement for frequencies $i = 0 \ldots$ maximum, and a number n of the segments or segment by segment Fourier transformations is determined for the segment by segment statistics such that by the conditions:

$$(m_n - m_{n-1})^2 \ll \epsilon$$

an adequate mean value stability and $$\Sigma(s_j - m_n)^2 > \delta$$

an adequate variance are provided for the segment by segment statistics with $m_n$ a mean value of the complex Fourier coefficient in the segment by segment statistics of the length n and $s_j$, a complex value of the Fourier coefficient in a repetition j with $j = 1 \ldots n$ and $\epsilon$ and $\delta$ as selected bounds.

12. Method according to claim 11, wherein optimum threshold values $\epsilon$ and $\delta$ are determined empirically.

13. Method according to claim 11 or 12, wherein the transmission function is determined from statistics of the form $[\Sigma(S_{ij} - m_j)^p] / [\Sigma(S_{ij} - m_j)^q]$ for all frequency lines $j = 1 \ldots$ maximum and for $i = 1 \ldots n$ segments, wherein for p and q condition $p > q$ applies and p and q are determined empirically.

14. Method according to claim 13, wherein additional higher-order moments or cumulants are determined.

15. Method according to claim 11 or 12, wherein median values are used as estimate values which are obtained by a complex differentiation or logarithmisation of a corresponding Fourier series and a sequence of coefficients derived therefrom, with a uniform size distribution over a frequency range.

16. Method according to claim 15, wherein additional higher-order moments or cumulants are determined.

17. Method according to claim 2 or 3, comprising:
 a) segmenting the measured signal from the patient,
 b) performing a complex Fourier transformation of the segments matched to segment length,
 c) determining segment by segment statistics of complex Fourier coefficients determined by the complex Fourier transformation,
 d) performing a logarithmic transformation of the segment by segment statistics and an estimation of corresponding statistics to be expected in an undistorted signal from the patient, and
 e) determining the transmission function from a difference in the logarithmic transformation of the segment by segment statistics.

18. Method according to claim 2 or 3, comprising:
 a) segmenting the measured signal from the patient,
 b) performing a complex Fourier transformation of the segments matched to segment length,
 c) determining segment by segment statistics on complex Fourier coefficients obtained from the complex Fourier transformation,
 d) differentiating a Fourier series formed from values of the segment by segment statistics as coefficients, and
 e) determining resonance and damping from the coefficients of the differentiated series.

19. Method according to claim 2 or 3, comprising segmenting of the measured signal from the patient and determination of a cepstrum.

20. Method according to claim 2, comprising an averaging of a plurality of consecutive determinations of the transmission function.

21. Method according to claim 20, comprising a weighted averaging or combination of a plurality of consecutive determinations of the transmission function in a statistical model.

22. Method according to claim 2, comprising a formal modelling of the transmission function determined consecutively as a space-state model.

23. Method according to claim 2, comprising a flattening interpolation of the transmission function or filtering of the transmission function by means of a low-pass filter.

24. Method according to claim 2, wherein after a reduction in noise in the spectral statistics expected from a ratio of the spectral statistics to statistics in an undistorted signal from the patient or a difference between the spectral statistics after a logarithmic transformation of the transmission function, a damping coefficient and a resonance frequency or an amount of the transmission function are determined for individual frequency lines.

25. Method according to claim 2, wherein a phase of the transmission function is calculated from the transmission function.

26. Method according to claim 2, wherein a phase of the transmission function is determined from further statistics of the form:
 a) $[\Sigma(S_{ij}-m_j)^p]/[\Sigma(S_{ij}-m_j)^q]$ for all frequency lines $j=1 \ldots$ maximum and for $i=1 \ldots n$ segments, wherein for p and q condition $p>q$ applies and p and q are determined empirically, or
 b) median values are used as estimate values which are obtained by a complex differentiation or logarithmisation of a corresponding Fourier series and a sequence of coefficients derived therefrom, with a uniform size distribution over a frequency range.

27. Method according to claim 2, wherein a complex inverse of the transmission function is determined by computer from amplitude and phase of the transmission function, the complex inverse serving as a correction data record for a correction in a frequency range, a segment by segment Fourier transformation of the measured signals from the patient taking place.

28. Method according to claim 1, wherein segmenting of a pressure signal from the patient measured invasively by means of a catheter system for invasive intra-arterial or intra-venal pressure measurement takes place heartbeat by heartbeat.

29. Method according to claim 1, comprising a coarsening of a spectral resolution by class formation for a plurality of frequency lines.

30. Method according to claim 1, comprising a direct adaptation to a second-order system with minimal deviation of a noisy transmission function determined from the spectral statistics.

31. Method according to any one of the preceding claims 20 to 24, comprising an iterative method for improving results.

* * * * *